(12) United States Patent
Marshall

(10) Patent No.: US 7,914,546 B2
(45) Date of Patent: Mar. 29, 2011

(54) LANCET

(75) Inventor: Jeremy Marshall, Oxford (GB)

(73) Assignee: Owen Mumford Limited, Oxford (GB)

( * ) Notice: Subject to any disclaimer, the term of this patent is extended or adjusted under 35 U.S.C. 154(b) by 463 days.

(21) Appl. No.: 10/518,513

(22) PCT Filed: Jun. 12, 2003

(86) PCT No.: PCT/GB03/02538
§ 371 (c)(1),
(2), (4) Date: Dec. 21, 2004

(87) PCT Pub. No.: WO04/000118
PCT Pub. Date: Dec. 31, 2003

(65) Prior Publication Data
US 2005/0240207 A1    Oct. 27, 2005

(30) Foreign Application Priority Data

Jun. 21, 2002  (GB) ................... 0214373.3

(51) Int. Cl.
*A61B 17/32*  (2006.01)
(52) U.S. Cl. ....................... 606/181; 206/365
(58) Field of Classification Search .......... 606/181–185, 606/167, 170; 600/583, 584; 206/363–365
See application file for complete search history.

(56) References Cited

U.S. PATENT DOCUMENTS

| | | | |
|---|---|---|---|
| 3,358,689 A * | 12/1967 | Higgins ................... | 606/181 |
| 4,545,376 A * | 10/1985 | Beiter ..................... | 606/181 |
| 5,366,469 A | 11/1994 | Steg et al. | |
| 5,385,571 A | 1/1995 | Morita | |
| 5,487,748 A * | 1/1996 | Marshall et al. ............. | 606/182 |
| 5,628,765 A * | 5/1997 | Morita ..................... | 606/182 |
| 6,168,606 B1 * | 1/2001 | Levin et al. ................ | 606/181 |

FOREIGN PATENT DOCUMENTS

| | | | |
|---|---|---|---|
| GB | 2 352 403 | | 1/2001 |
| GB | 2352403 A | * | 1/2001 |
| JP | 5-285127 | | 11/1993 |
| JP | 6-22941 | | 2/1994 |
| JP | 8-597 | | 1/1996 |

OTHER PUBLICATIONS

Japanese Patent Office Notice of Reasons for Rejection, dated May 26, 2009 and issued in corresponding Japanese Patent Application No. 2004-515001.
Japanese Office Action dated Jun. 29, 2010 from corresponding JP2004-515001.

* cited by examiner

*Primary Examiner* — Todd E Manahan
*Assistant Examiner* — Kathleen Sonnett
(74) *Attorney, Agent, or Firm* — Young & Thompson

(57) ABSTRACT

Plastics material injected through an entry point of a mould at the location (8) is caused to deflect around a pin which creates the hole (14) in a guard (5), so as to increase the balance of flow of material to either side of the pin (9). In order to minimize the tendency for the plastics material to bend out of shape the tip of the needle embedded within an enlarged portion (13) the mould is formed such that the mould material is initially encouraged to divide and flow through outer thickened regions (10) surrounding a thinner portion. At point (12) the plastics material is therefore caused to slow down resulting in greater equalization of the flow speed of the plastics material to either side of the needle tip.

8 Claims, 1 Drawing Sheet

LANCET

BACKGROUND OF THE INVENTION

1. Field of the Invention

Figure 1:
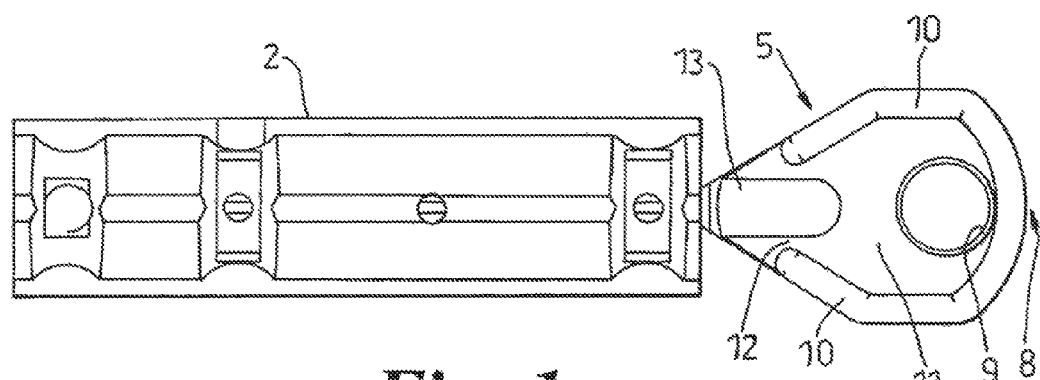

A lancet with a removable guard is located over the point of a needle part of a lancet.

2. Description of the Related Art

A conventional lancet comprises a needle held by a support body that has been moulded about the needle. In one form of lancet, a removable guard is moulded at the same time to cover the point of the needle. The guard can be snapped away to expose the needle for use. Conventional moulding techniques tend to subject the needle tip to a bending force so that it can be deflected to one side and thus becomes offset from the body. This can be a major disadvantage when the lancet is used in conjunction with an automatic finger pricking device, where the lancet is held by its body and the needlepoint is driven through a small hole in a support platform held against the blood-sampling site. Any misalignment of the needle could cause increased discomfort during the pricking operation. Also, recent diagnostic techniques may include a blood collecting test strip at the sampling site, so it is important to prevent any misalignment of the needle tip to avoid contact between the needle tip and the support platform, or between the needle tip and the wrong part of the test strip.

SUMMARY OF THE INVENTION

It is the object of this invention to alleviate the problem of the bending of the needle tip.

Accordingly this invention provides a lancet with a removable guard located over the point of a needle part of the lancet, the guard being formed from a moulded plastics material with an outer edge thickened region leading from the end of the guard remote from the needle point to a thinner section of the plastics material approaching the needle point.

When forming the lancet in this way, during the moulding process, the plastics material is caused to be slowed temporarily as it meets the interface between the outer edge thickened region and the thinner section approaching the needle tip. Ideally the guard will be formed with a centrally positioned hole close to the end of the guard remote from the needle point. This hole will be created by a pin forming part of the mould for creating the guard. During the moulding process the plastics material will be caused to flow around the central pin. This helps to create a more even flow to both sides of the guard. Consequently, during manufacture, the needle tip will be subjected to controlled balanced forces which act behind the needle point, subjecting it to a lower bending force than with conventional procedures.

Ideally the plastics material forms a further thickened region about the needle tip, but separated from the outer edge region by said thinner section. This is to protect the needle tip from being accidentally being displaced through the side of the plastics material prior to use. Although the needle tip itself will be surrounded by a thickened region of material, the slowing down of the material in the thinner section will be sufficient to limit the potential for a bending force to be applied to the needle tip.

Ideally the guard will be of generally tab-like form, with the thickened region forming arc-like portions on the two side edges of the guard. The guard can be interconnected with a support body holding the needle via a breakable neck portion moulded with the guard and the support body.

The invention also extends to a method of forming a lancet in which a needle is held in a mould formed to create a support body for holding the base portion of the needle and a removable guard about the pointed needle tip, the mould having an entry point for plastics material, at the end of the guard remote from the needle point, leading to an outer edge thickened hollow region which in turn leads to a thinner hollow section approaching the needle tip and plastics material is injected into the mould via the entry point to create the guard about the needle tip.

In the preferred performance of the method the plastics material flows around both sides of a pin located close to said entry point towards said edge thickened hollow region and ideally may flow into an enlarged hollow region surrounding the needle tip from said thinner hollow section. It is preferred that the plastics material flows from the guard through a neck portion of the mould leading to the part of the mould defining the support body.

BRIEF DESCRIPTION OF THE DRAWING FIGURES

The invention may be performed in various ways and a preferred embodiment thereof will now be described in reference to the accompanying drawings, in which:—

Figure 2:
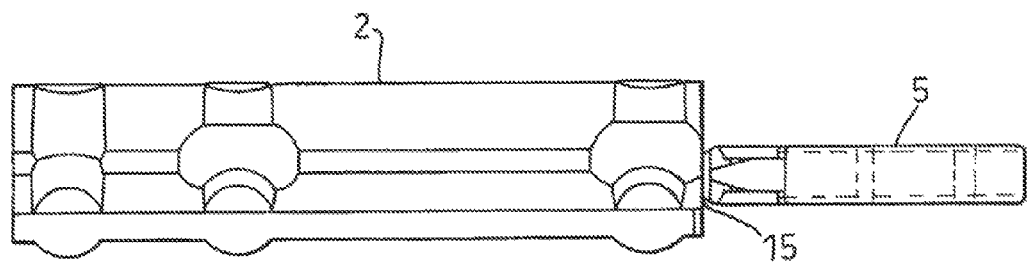
Figure 3:
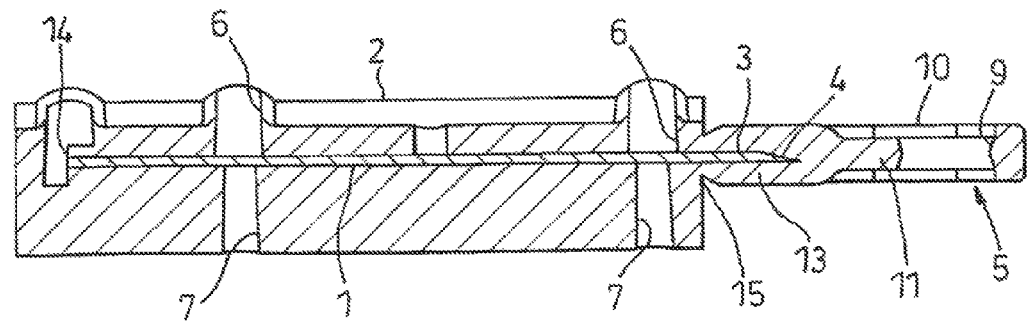

FIGS. 1 and 2 are plan, side views respectively of a lancet of this invention; and FIG. 3 is a vertical section through the lancet of FIGS. 1 and 2.

DETAILED DESCRIPTION OF THE PREFERRED EMBODIMENTS

The lancet shown in the drawings incorporates a needle 1 (FIG. 3) held within a support body 2. The tip portion 3 of the needle (having an angled point 4) is protected by a guard 5. The support body 2 and the guard 5 are moulded simultaneously about the needle 1. During moulding the needle is held by pins which create passageways 6 and 7 within the support body 1. The plastics material is injected through an entry point of the mould at the location 8 and is caused to deflect around a pin which creates the hole 9 in the guard 5, so as to increase the balance of flow of material to either side of the pin 9. Conventionally several lancets are moulded at one time to either side of a spine. The plastics material therefore enters at the location 8 at an angle and tends to bend around the far corner of the part of the mould defining the lancet such that there will be an uneven flow of pressure on to the two sides of the end portion 3 of the needle which can tend to bend it, particularly when the plastics material hits the angled face 4. There is then the possibility that the tip 3 will be bent out of shape within the guard 5 which can make the lancet more difficult to use with a finger pricker device when the guard has been removed.

In order to minimise the tendency for the plastics material to bend the tip 3 of the needle out of shape, the mould is formed such that the mould material is initially encouraged to divide and flow through outer thickened regions 10. These surround a thinner portion 11 with the thickened portion 10 terminating before it reaches the region of the needle tip 3. At this point 12 the plastics material is therefore caused to slow down resulting in greater equalisation of the flow speed of the plastics material to either side of the needle tip 3. Immediately around the needle tip 3 however the mould is formed to create a thickened region 13 to provide adequate protection for the needle tip. Although the flow of plastics material is slowed by the narrow portion 12, there is still sufficient force (although now much more evenly distributed about the needle tip 3) to push the needle back against a rear stop (which creates the hole 14) in the support body 2 to ensure that the projecting part of the needle 1 is of a required length.

In use the guard 5 is twisted to shear the material about a neck 15 so that the guard can be removed to expose the needle tip 3 for use. The moulding method employed which, in particular, creates the narrowed portion 12 between the thickened outer edge regions 10 and the thickened region 13 surrounding the needle tip 3, helps to ensure that the exposed needle tip is unlikely to be in a bent condition when the guard 5 is detached.

The invention claimed is:

1. A lancet, comprising:
   a needle having a pointed tip;
   a support body enclosing the needle such that the pointed tip projects beyond the end of the support body;
   a removable guard located over the pointed tip of the needle, said guard having been integrally moulded from plastics material with said support body and connected thereto by a breakable neck portion;
   said removable guard portion having an outer peripheral thickened rib describing a generally U- or C-shape, a central region of thinner section than said rib and partly surrounded by said rib and a further tip encasing region encasing the tip of the needle, the tip encasing region being of thicker section than said central region and being spaced from adjacent ends of the peripheral thickened rib such that there are respective gaps therebetween bridged only by said thinner central section, said thinner central section and said peripheral thickened rib substantially surrounding said tip encasing region and the tip.

2. The lancet according to claim 1, wherein the guard is formed with a centrally positioned hole close to an end of the guard remote from the needle point.

3. The lancet according to claim 2, wherein the guard is of generally tab-like form, with the thickened rib forming arc-like portions on two side edges of the guard which lead to the thinner section of plastics material adjacent to the needle tip.

4. The lancet according to claim 1, wherein the guard is of generally tab-like form, with the thickened rib forming arc-like portions on two side edges of the guard which lead to the thinner section of plastics material adjacent to the needle tip.

5. A lancet, comprising:
   a needle having a pointed tip;
   a support body enclosing the needle such that the pointed tip projects beyond an end of the support body;
   a removable guard located over the pointed tip of the needle, said guard having been integrally moulded from plastics material with said support body and connected thereto by a breakable neck portion;
   said removable guard portion having an outer peripheral thickened rib describing a generally U- or C-shape with ends of the peripheral thickened rib being disposed laterally adjacent said needle, a central region of thinner section than said rib and partly surrounded by said rib and a further tip encasing region encasing the tip of the needle, the tip encasing region being of thicker section than said central region and being spaced from the adjacent ends of the peripheral thickened rib such that there are respective gaps therebetween bridged only by said thinner central section, said thinner central section said peripheral thickened rib substantially surrounding said tip encasing region and the tip.

6. A method of forming a lancet, comprising:
   holding a needle in a mould formed to create a support body for holding a base portion of the needle and a removable guard about a pointed needle tip and to form a breakable neck portion between the support body and the guard, the mould having an entry point for plastics material, at an end of the guard remote from the needle point, leading to an outer peripheral thickened hollow rib of generally U- or C-shape which in turn leads to a thinner hollow section approaching the needle tip and a further enlarged hollow region encasing the needle tip, the hollow region encasing the needle tip being of thicker section than said thinner hollow section, the further enlarged hollow region being spaced from adjacent ends of the peripheral thickened hollow rib to leave respective gaps therebetween that are bridged by said thinner hollow section, the thinner hollow section said peripheral thickened hollow rib substantially surrounding said enlarged hollow region encasing the needle tip and the tip; and
   injecting plastics material into the mould via the entry point to create the guard about the needle tip.

7. The method according to claim 6, wherein the plastics material flows around both sides of a pin located close to said entry point towards said edge thickened hollow region.

8. The method according to claim 6, wherein the ends of the peripheral thickened rib are disposed laterally said needle.

* * * * *